(12) United States Patent
Reetz et al.

(10) Patent No.: US 6,583,305 B1
(45) Date of Patent: Jun. 24, 2003

(54) FERROCENE-BASED DIPHOSPHONITES FOR ASYMMETRICAL CATALYSIS

(75) Inventors: Manfred T. Reetz, Mülheim an der Ruhr (DE); Andreas Gosberg, San Diego, CA (US)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/786,382

(22) PCT Filed: Aug. 21, 1999

(86) PCT No.: PCT/EP99/06153

§ 371 (c)(1),
(2), (4) Date: Jun. 8, 2001

(87) PCT Pub. No.: WO00/14096

PCT Pub. Date: Mar. 16, 2000

(30) Foreign Application Priority Data

Sep. 4, 1998 (DE) ......................................... 198 40 279

(51) Int. Cl.⁷ .......................... C07F 17/00; C07F 19/00; B01J 31/00; C07C 5/03
(52) U.S. Cl. .............................. 556/14; 556/20; 556/28; 568/1; 568/7; 585/275; 502/155; 502/156
(58) Field of Search .............................. 556/20, 14, 28; 585/275; 568/1, 7; 502/155, 156

(56) References Cited

U.S. PATENT DOCUMENTS 5,171,892 A 12/1992 Burk ........................... 568/12
5,817,850 A * 10/1998 Pastor et al. .................. 556/14

OTHER PUBLICATIONS

Nifant'ev et al., Russian Journal of General Chemistry, vol. 65, No. 1, pp. 682–685 (1995).*

Eric Oosterom, G. et al.: "Catalysis in the core of Carbosilane dendrimer"; Chem Commun. (Cambridge) (1999) (12) 1119–1120.

Reetz, Manfred T. et al: "Diphosphonits as highly efficient ligands for enatioselective rhodium–catalyzed hydrogenation", Chem. Commun. (Cambridge) (1998), (19), 2077–2078.

Nifant' Ev, I.E., et al: "Ferrocenylene diphosphonites as ligands in the synthesis of oligonuclear heterometallic complexes", Zh. Obshch. Khim. (1995) (65(5), 756–60.

Burk, Mark J. et al: "New Chiral 1,1'–bis(phospholano)ferrocene ligands for asymmetric catalysi" Tetrahedron Lett (1994), 35(50), 9363–6.

* cited by examiner

Primary Examiner—Porfirio Nazario-Gonzalez
(74) Attorney, Agent, or Firm—Norris McLaughlin & Marcus

(57) ABSTRACT

The present invention relates to novel chiral 1,1'-ferrocenylene diphosphonites and the synthesis thereof, in addition to complexes of said compounds with metals from groups VIIb, VIIIb and Ib of the Periodic Table and to the use thereof for enantioselective hydrogenation of olefins, ketones and imines, or enantioselective hydroboration and 1,4-addition to activated olefins.

24 Claims, No Drawings

FERROCENE-BASED DIPHOSPHONITES FOR ASYMMETRICAL CATALYSIS

This application is a 371 of PCT/EP99/06153, which was filed on Aug. 21, 1999.

The present invention relates to novel chiral 1,1'-ferrocenylene diphosphonites and the synthesis thereof, in addition to complexes of said compounds with metals from groups VIIb, VIIIb and Ib of the Periodic Table and to the use thereof for enantioselective hydrogenation of olefins, ketones and imines.

In the last 20 years, the catalytic enantioselective synthesis has gained importance in industry, e.g., the transition-metal catalyzed asymmetric hydrogenation (B. Cornils, W. A. Herrmann, Applied Homogeneous Catalysis with Organometallic Compounds, Wiley-VCH, Weinheim, 1996; R. Noyori, Asymmetric Catalysis in Organic Synthesis, Wiley, New York, 1994). Rhodium, ruthenium or iridium complexes of optically active diphosphanes such as BINAP (R. Noyori et al., J. Am. Chem. Soc. 1980, 102, 7932), DuPHOS (M. J. Burk et al., J. Am. Chem. Soc. 1995, 117, 9375), BICP (X. Zhang et al., J. Am. Chem. Soc. 1997, 119, 1799) and BPE (M. J. Burk et al., J. Am. Chem. Soc., 1996, 118, 5142) are usually used as catalysts. Drawbacks in these systems include the relatively high preparative expenditure in the preparation and, if necessary, optical resolution of the racemic ligands and the frequently insufficient enantioselectivity observed in catalysis. Therefore, it has been the object of industrial and academic research to prepare novel and particularly well-performing ligands in as simple a way as possible.

In contrast to diphosphanes, chiral diphosphonites as ligands in catalysis have been described only in two cases (L. Dahlenburg et al., J. Organomet. Chem. 1998, 564, 227, and Eur. 3. Inorg. Chem. 1998, 1, 885, and I.E. Nifant'ev et al., Russ. J. Gen. Chem. 1995, 65, 682.).

In the first case, diphosphonites were used which are derived from optically pure 1,2-bis(dichlorophosphino)cyclopentane and achiral monovalent alcohols or optically pure (R)-binaphthol. In the rhodium-catalyzed hydrogenation of 2-acetamidocinnamic acid, a maximum enantiomeric excess of 78% could be achieved using such ligands in the case of the corresponding phenol-derived diphosphonite. The substrate-to-catalyst ratios used were extremely low in all cases (76:1). In addition, it is pointed out that there are significant preparative difficulties in the preparation of the rhodium complexes of these ligands. These are two serious drawbacks preventing practicability.

Nifant'ev et al. used ferrocenylene diphosphonites based on protected monosaccharides, namely $C_1$-symmetric aliphatic 1,2-diols (2 examples) and 1,3-diols and $C_2$-symmetric aliphatic 1,4-diols (1 example each). Rhodium complexes of these ligands were synthesized from $[Rh(CO)_2Cl]_2$ as a precursor and employed in the asymmetric hydrosilylation of acetophenone. The highest value of enantiomeric excess achieved was 32%, chemoselectivity also being insufficient, so that commercial usefulness can be excluded.

However, according to our results, ferrocenylene diphosphonites are ligands having excellent properties when suitable chiral diols are selected as the starting materials. In addition, they can be prepared very easily and inexpensively. It was found that useful diols primarily include $C_2$-symmetric aliphatic 1,2-diols or axially chiral aromatic or heteroaromatic diols. Thus, not only the selection of a suitable backbone, ferrocene in the present case, but also the selection of suitable diols is essential for a successful application of diphosphonites. The two examples known to date from the literature (see above) left this point unconsidered, so that practicable results could not be achieved to date. The present invention includes the first example of chiral diphosphonites in general with which enantioselectivities of more than 99% in asymmetric catalysis and thus selectivities useful for practical applications can be achieved.

The basic idea of the present invention includes chiral $C_2$-symmetric diphosphonites with ferrocene as the backbone containing either chiral $C_2$-symmetric 1,2-diols with an aliphatic base structure or axially chiral aromatic or heteroaromatic diols in the P/O heterocycle, and their synthesis. The invention also includes metal complexes of such ligands and their use in asymmetric synthesis. Ligands of this type exhibit excellent enantioselectivities in the hydrogenation of various prochiral olefins, but can be prepared clearly more simply and therefore less expensively as compared to systems known to date from the literature having a comparably high selectivity (e.g., DuPHOS or PennPHOS; M. J. Burk et al., J. Am. Chem. Soc. 1995, 117, 9375, and X. Zhang et al., Angew. Chem. 1998, 110, 1203).

In detail, the invention comprises 1,1'-ferrocenylene diphosphonites of types I, II, III and IV.

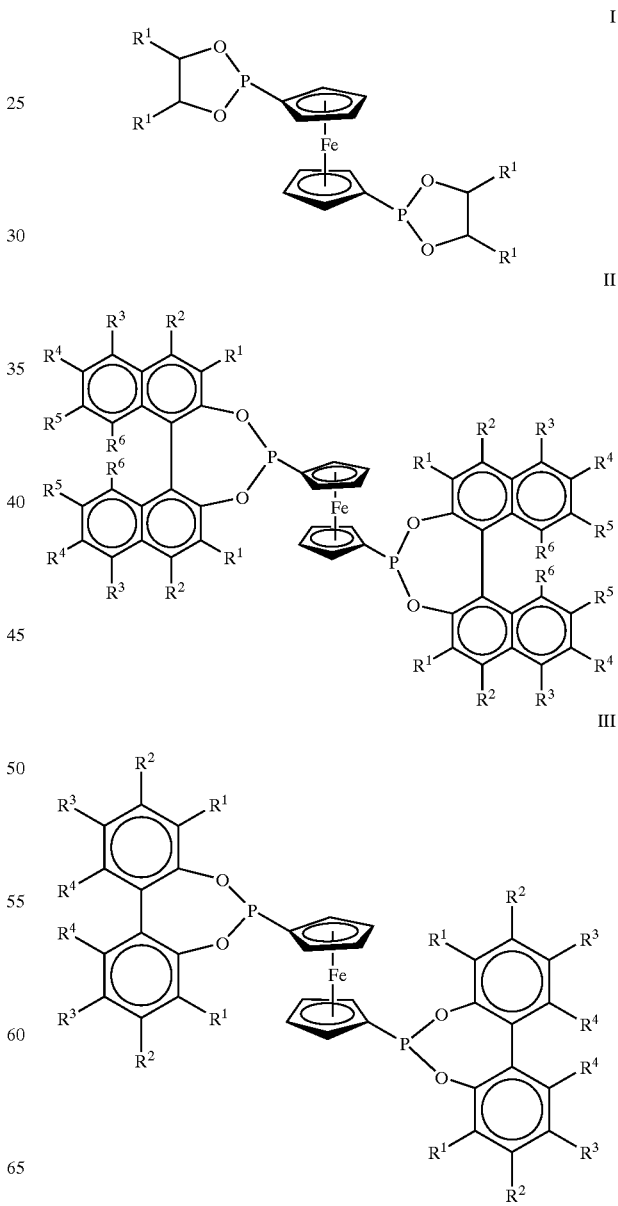

-continued

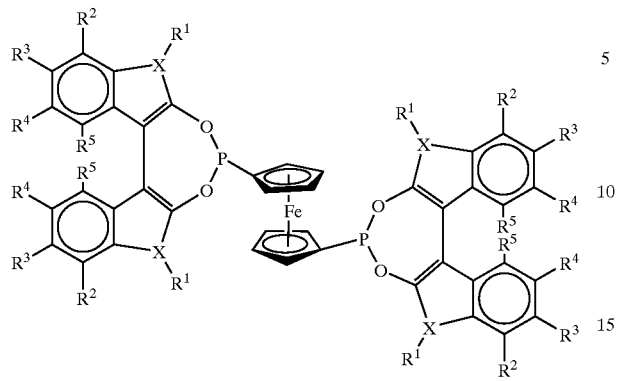

IV

In the case of class I of compounds, the building blocks are $C_2$-symmetric chiral diols of type V.

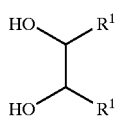

V

Residue $R^1$ can be a saturated hydrocarbon which may optionally be functionalized, such as in the case of 1,2-diol units of protected carbohydrates or protected aminoalcohols. Possible residues also include aromatic or heteroaromatic groups, such as phenyl, naphthyl or pyridyl, which can themselves be functionalized as desired. Finally, it is possible for the residues to consist of ester or amide groups, such as $—CO_2CH_3$, $—CO_2C_2H_5$, $—CO_2—i—C_3H_7$ or $—CO[N(CH_3)_2]$, $—CO[N(C_2H_5)_2]$ or $—CO[N(i—C_3H_7)_2]$, the corresponding diols V being tartaric acid derivatives.

In the case of class II of ligands, the oxygen-containing building block consists of binaphthol VI with residues $R^1$, $R^2$, $R^3$, $R^4$, $R^5$ and $R^6$, which may independently represent the following groups: hydrogen (H), saturated hydrocarbons, optionally functionalized and/or bridging (e.g., $R^1+R^2=—(CH_2)_4—$), aromatic or heteroaromatic groups which may also be functionalized and/or condensed and thus represent cyclic residues (for example, $R^1+R^2=$ ortho-phenylene; corresponding to 4,4'-dihydroxy-5,5'-bis(phenanthryl)), non-aromatic unsaturated hydrocarbons, such as alkynyl groups $—C≡CR$, which may also be functionalized, silyl groups, such as $—SiMe_3$, halogens (—Cl, —Br, —F, —I), nitro ($—NO_2$) or nitrile (—CN) groups, or esters ($—CO_2R$), amides (—C(O)NRR'), amines (—NRR'), ethers (—OR), sulfides (—SR) and selenides (—SeR), wherein R and R' are hydrogen, saturated or non-aromatic unsaturated hydrocarbons which may optionally be functionalized, or aromatic residues which may optionally be functionalized. In particular, the present invention includes all combinations of the residues mentioned for $R^1$, $R^2$, $R^3$, $R^4$, $R^5$ and $R^6$ including all $C_1$- and $C_2$-symmetric substitution patterns of the binaphthol base structure. Further, one or more carbon atoms of the binaphthol core may also be replaced by heteroatoms, such as nitrogen. Preferably, binaphthol ($R^1=R^2=R^3=R^4=R^5=R^6=H$) itself serves as a building block.

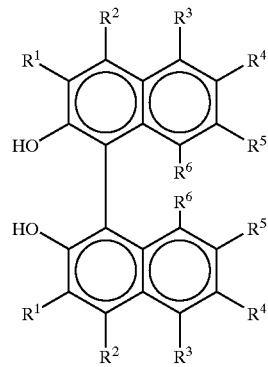

VI

In the case of class III of compounds, the dihydroxy building block is a functionalized, configuratively stable biphenol VII. Configurative stability with respect to axial chirality is ensured when $R^4≠H$ (E. L. Eliel, S. H. Wilen, L. N. Mander, Stereo-chemistry of Organic Compounds, Wiley, New York, 1994). $R^1$ to $R^4$ have the same range of variation as residues $R^1$ to $R^6$ in the case of class VI of compounds. Preferably, however, $R^1=R^2=H$, and $R^3+R^4=—(CH_2)_4—$ (2,2'-dihydroxy-5,5',6,6',7,7',8,8'-octahydro-1,1'-binaphthyl, D. J. Cram et al., J. Org. Chem. 1978, 43, 1930).

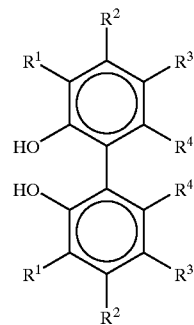

VII

In the case of class IV of compounds, the dihydroxy building block is a functionalized, configuratively stable heteroaromatic system VIII derived from 2,2'-dihydroxy-3,3'-bis(indolyl) (X=N), 2,2'-dihydroxy-3,3'-bis(benzo[b]thiophenyl) (X=S) or 2,2'-dihydroxy-3,3'-bis(benzo[b]furanyl) (X=O). In these cases too, the substituents have the same range of variation as in VI. Substituent $R^1$ is absent in the cases where X=O or X=S.

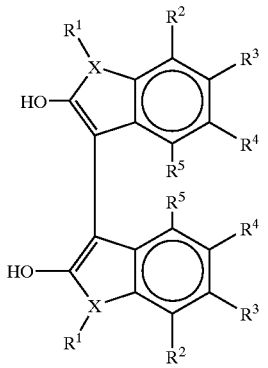

VIII

The present invention encompasses all stereo-isometric forms of diols V, VI, VII and VIII as building blocks.

Scheme 1 illustrates the synthetic path for the ligands according to the invention. In thie first step, a twofold lithiation of ferrocene with n.-butyllithium in the presence of tetramethylethylenediamine (TMEDA) as known from the literature (J. J. Bishop et al., J., Organomet. Chem. 1971, 27, 241) is effected, followed by phosphorylation with phosphorus chlorides, such as $CIP[N(CH_3)_2]_2$ or $CIP[N(C_2H_5)_2]_2$, to form class IX of compounds; in the second step, these are reacted with diols V, VI, VII or VIII to form the ligands I, II, III or IV, respectively.

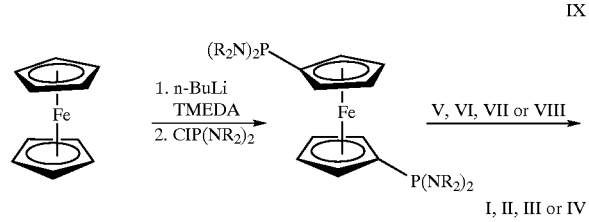

Scheme 1

A variant of this synthesis includes an additional step, i.e., the reaction of IX with HCl to form X, which is then reacted with diols V, VI, VII or VIII (Scheme 2). In many cases, this increases the overall yield.

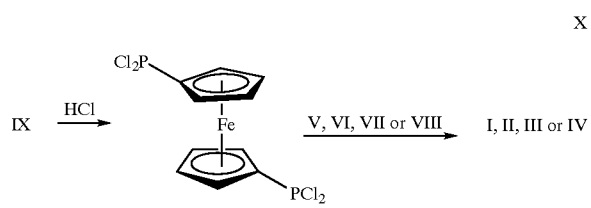

Scheme 2

The invention also includes the formation of novel metal complexes by reacting the ligands according to the invention with transition metal compounds usually employed with diphosphines, especially metals of Periodic Table groups VIIb, VIIIb and Ib (see, e.g., B. Cornils, W. A. Herrmann, Applied Homogeneous Catalysis with Organometallic Compounds, Wiley-VCH, Weinheim, 1996; R. Noyori, Asymmetric Catalysis in Organic Synthesis, Wiley, New York, 1994). Examples include Rh, Ru, Ir, Ni, Pd or Cu complexes of types XI-XXXVIII (wherein cod stands for $\eta^2:\eta^2$-1,5-cyclooctadiene, and cymol stands for $\eta^6$-1-isopropyl-4-methylbenzene).

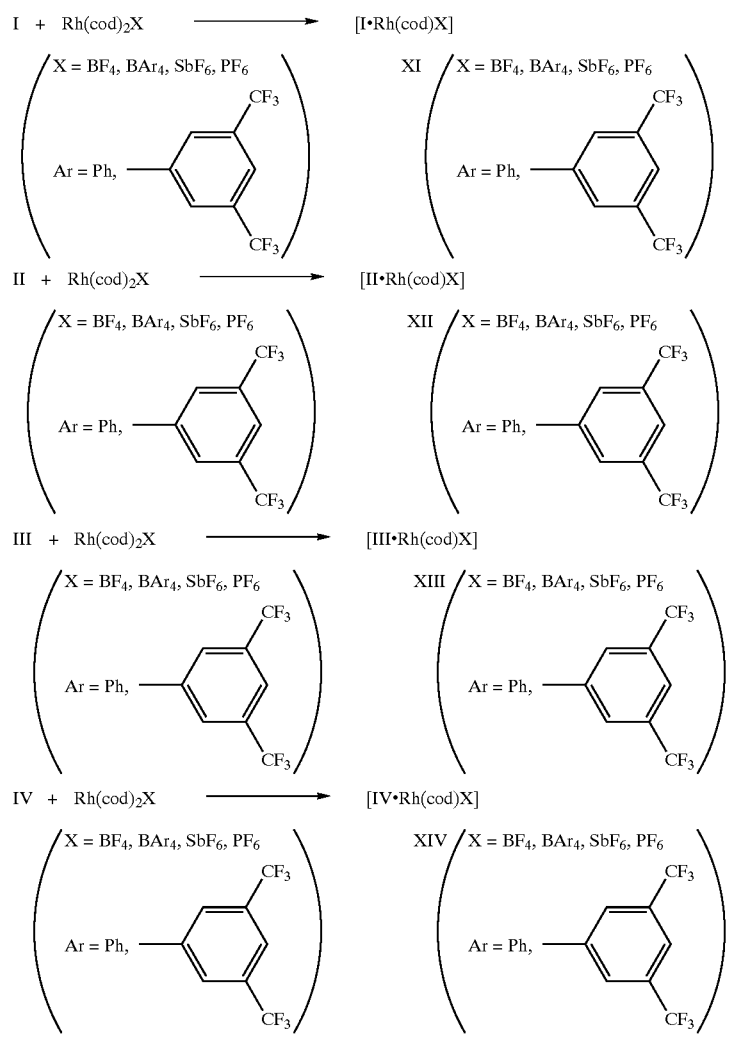

-continued
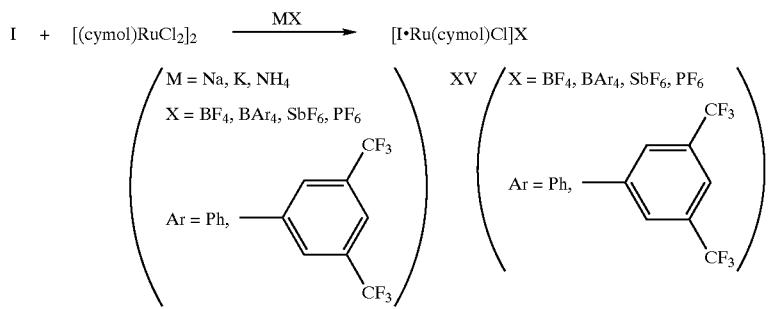
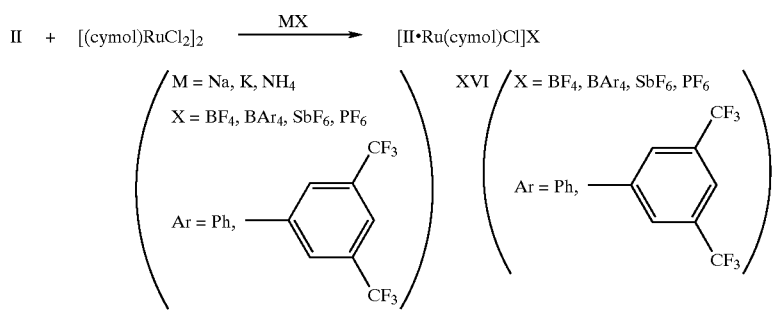
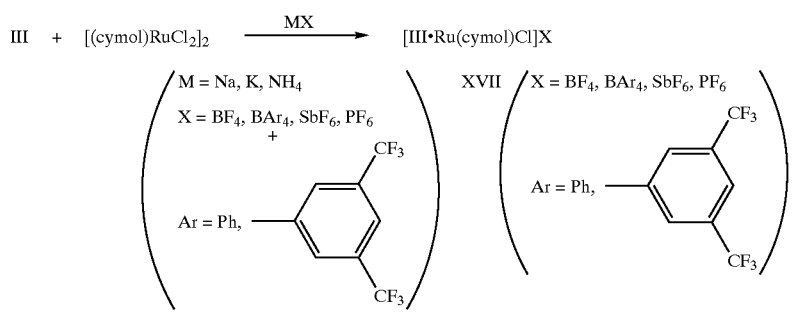
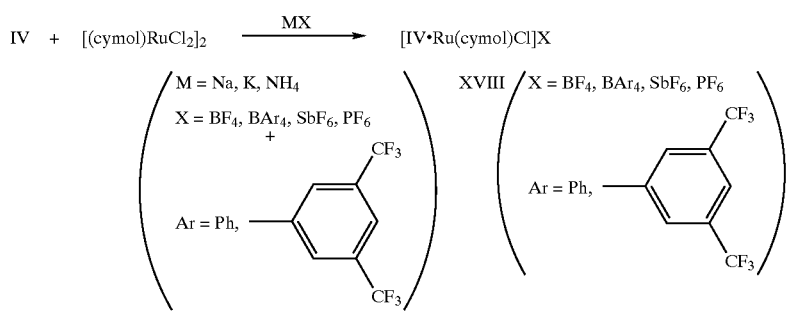
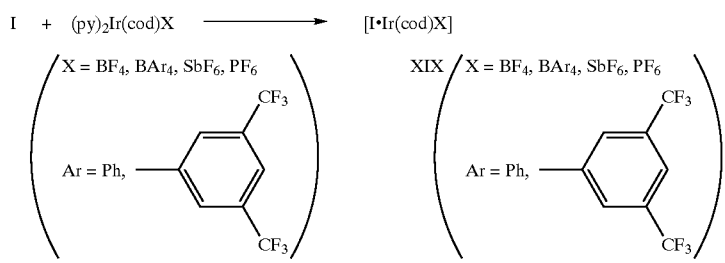

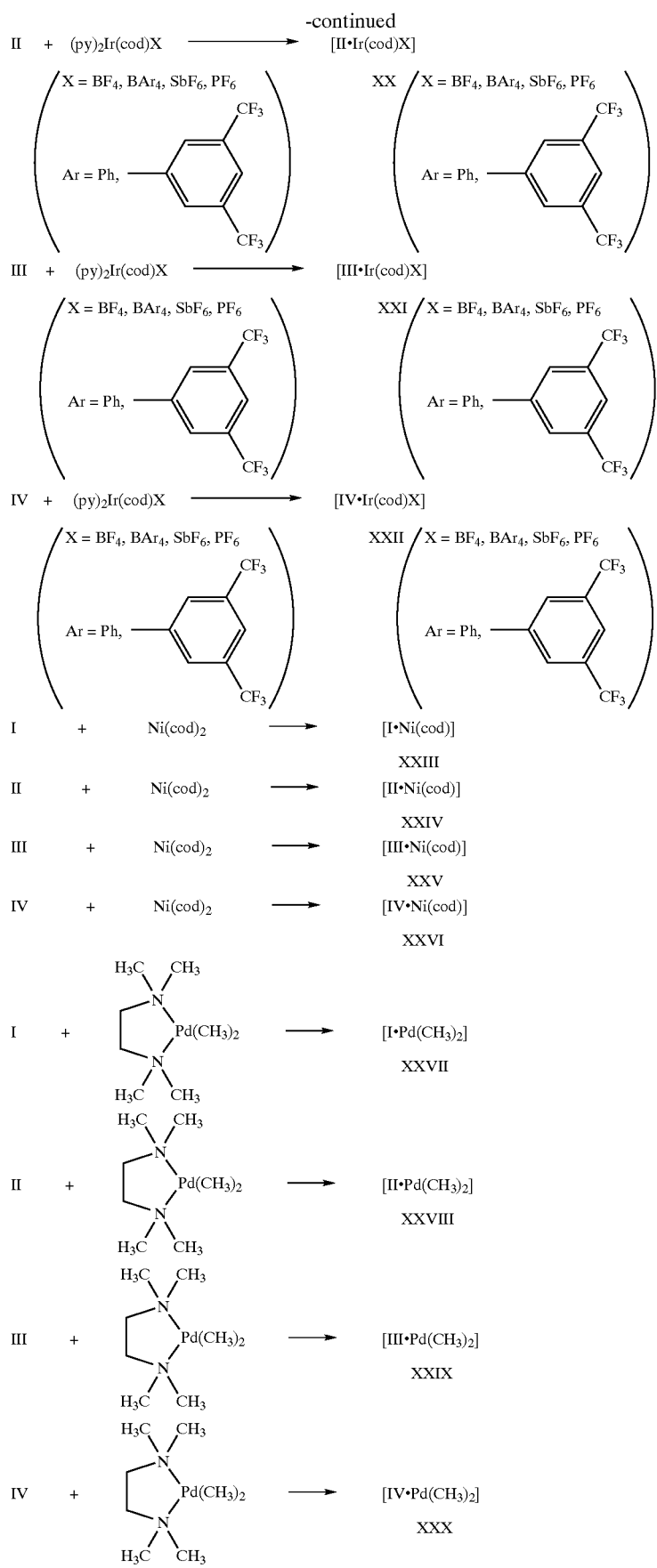

-continued

| | | | | | |
|---|---|---|---|---|---|
| I | + | CuOTf | → | [I·CuOTf] | |
| | | (Tf = SO$_2$CF$_3$) | | XXXI | (Tf = SO$_2$CF$_3$) |
| II | + | CuOTf | → | [II·CuOTf] | |
| | | (Tf = SO$_2$CF$_3$) | | XXXII | (Tf = SO$_2$CF$_3$) |
| III | + | CuOTf | → | [III·CuOTf] | |
| | | (Tf = SO$_2$CF$_3$) | | XXXIII | (Tf = SO$_2$CF$_3$) |
| IV | + | CuOTf | → | [IV·CuOTf] | |
| | | (Tf = SO$_2$CF$_3$) | | XXXIV | (Tf = SO$_2$CF$_3$) |
| I | + | Cu(OTf)$_2$ | → | [I·Cu(OTf)$_2$] | |
| | | (Tf = SO$_2$CF$_3$) | | XXXV | (Tf = SO$_2$CF$_3$) |
| II | + | Cu(OTf)$_2$ | → | [II·Cu(OTf)$_2$] | |
| | | (Tf = SO$_2$CF$_3$) | | XXXVI | (Tf = SO$_2$CF$_3$) |
| III | + | Cu(OTf)$_2$ | → | [III·Cu(OTf)$_2$] | |
| | | (Tf = SO$_2$CF$_3$) | | XXXVII | (Tf = SO$_2$CF$_3$) |
| IV | + | Cu(OTf)$_2$ | → | [IV·Cu(OTf)$_2$] | |
| | | (Tf = SO$_2$CF$_3$) | | XXXVIII | (Tf = SO$_2$CF$_3$) |

Finally, the invention also includes the use of the metal complexes according to the invention as catalysts in asymmetric catalysis, such as hydrogenation, hydroformylation, hydrocyanation, hydrosilylation, hydrovinylation, hydroboration and copper-catalyzed 1,4-addition. Examples include the asymmetric hydrogenations of dimethyl itaconate XXXIX, 2-acetamidomethyl acrylate XL, (Z)-2-acetamidocinnamic acid XLI and its methyl ester XLII, α-acetamidostyrene XLIII and N-(1-phenylethylidene) aniline XLIV, which can be performed with very high chemical yields and enantioselectivities when the metal complexes according to the invention are used. The same applied to the hydroboration of styrene VL, and the copper-catalyzed 1,4-addition to 2-cyclohexene-1-one VLI or 2-cycloheptene-1-one VLII.

These results are of high practical relevance, which makes these compounds interesting for industrial applications as well.

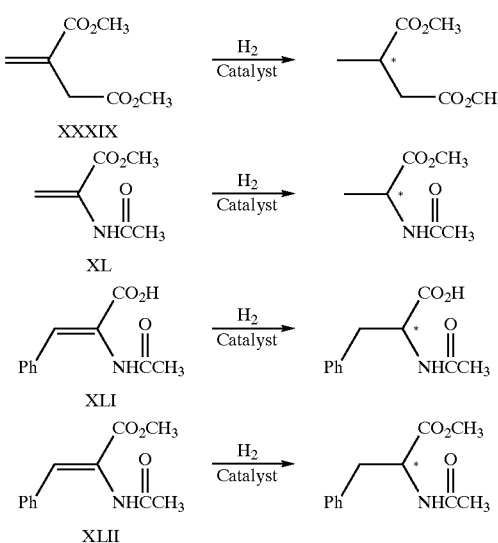

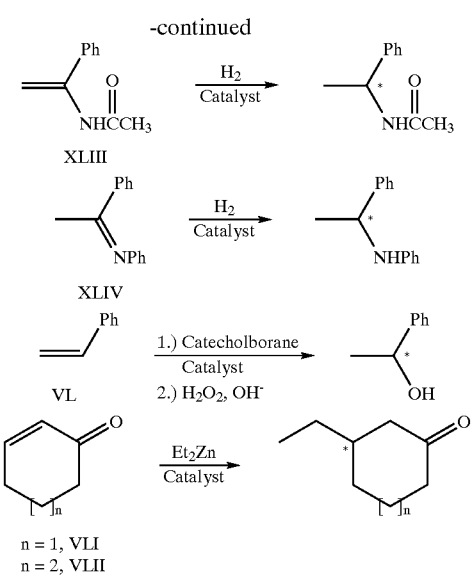

EXAMPLE 1

Synthesis of 1,1'-bis[bis(diethylamino)phosphino] ferrocene (IX, R=Et)

At room temperature, 30.0 g (0.161 mol) of ferrocene in 600 ml of absolute hexane is charged in a vessel. A mixture of 250 ml (0.40 mol) of 1.60 M n-butyllithium solution in hexane and 63.0 ml (48.5 g, 0.417 mol) of abs. N,N,N',N'-tetramethylethylenediamine is added dropwise at room temperature within 40 min. The mixture is allowed to stir at room temperature over night. The precipitated orange solid is filtered off through a P4 reverse frit and thoroughly washed with pentane until the filtrate remains colorless. The filtration residue is subsequently dried in an oil pump vacuum to obtain 37.7 g (0.12 mol, 75%) of N,N,N',N'-tetramethylethylenediamino-1,1'-dilithioferrocene as a fine orange powder.

At −78° C., 11.7 g (37.2 mmol) of this powder is suspended in 300 ml of abs. THF. A solution of 20.0 ml (92.3 mmol) of bis(diethylamino)chlorophosphine in 50 ml of abs. THF is added dropwise within 1 h. The mixture is allowed to thaw to room temperature and stirred for another 15 h. The solution, which has now a red-brown color, is freed from the solvent, and the oily residue is taken up in 300 ml of abs. pentane. The undissolved lithium chloride is separated off by filtration through a P4 frit with Celite 545® as a filtering aid. The clear filtrate is again completely freed from solvent. The oily red-brown residue is subjected to fractional distillation at $10^{-6}$ mbar. Under these conditions, the product distills at a head temperature of 175–190° C. to obtain 18.4 g (34.7 mmol, 93%, calculated on the basis of the N,N,N',N'-tetramethylethylenediamino-1,1'-dilithioferrocene employed) of a very viscous red-brown oil. Analytical results: $^1$H NMR (d$_6$-C$_6$H$_6$, 300 MHz): 4.13 (t)J =1.8 Hz [4H], 4.10 (m) [4H], 2.81 (m) [16H], 0.81 (t) $^3$J$_{H\text{-}H}$=7.2 Hz [24H]; $^{13}$C{$^1$H} NMR (d$_6$-C$_6$H$_6$, 75 MHz): 82.1 (d) J$_{C\text{-}P}$=11.9, 72.9 (dd) J$_{C\text{-}P}$=2.6 Hz, 9.8 Hz, 72.5 (dd) J$_{C\text{-}P}$=2.3 Hz, 4.4 Hz, 43.1 (d) $^2$J$_{C\text{-}P}$=17.4 Hz, 15.2 (d) $^3$J$_{C\text{-}P}$=3.2 Hz; $^{31}$P NMR (d$_6$-C$_6$H$_6$, 121 MHz): 91.6 (s); MS (EI, pos. ions): m/z=534 [M$^+$] (30%), 463 [M+-C$_4$H$_9$N] (14%), 391 (72%), 320 (100%), 247 (25%), 195 (25%), 128 (11%), 104 (10%); HRMS (EI, pos. ions): found: 534.270322±0.000625, expected: 534.270361; IR (capillary): $\tilde{V}$ (cm$^{-1}$)=3097 (w), 2965 (s), 2929 (m-s), 2850 (m-s), 1461 (m), 1373 (s), 1342 (w), 1291 (m-w), 1187 (s), 1100 (w), 1072 (m-w), 1023 (s), 1012 (s), 908 (s), 792 (m-s), 662 (s-m).

EXAMPLE 2

Synthesis of 1,1'-bis(dichlorophosphino)ferrocene (X)

At –78° C., 8.63 g (16.3 mmol) of 1,1'-bis[bis (diethylamino)phosphino]ferrocene (IX, R=Et) in 400 ml of abs. diethyl ether is charged in a vessel. A solution of 40 ml of 3.9 M HCl in abs. diethyl ether in 150 ml of diethyl ether is added dropwise within 2 h. After the addition is complete, the mixture is allowed to warm to room temperature and stirred over night to obtain an orange solution containing a colorless solid suspended therein, which is separated off by filtration through a P4 frit with Celite 545® as a filtering aid. The clear orange filtrate is then completely freed from solvent. The orange solid is subsequently recrystallized from 30 ml of a mixture of abs. toluene/pentane (1:1) to obtain 5.94 g (15.3 mmol) of product X (94%) in the form of coarse acicular crystals. Analytical results: $^1$H NMR (d$_6$-C$_6$H$_6$, 300 MHz): 4.66 ppm (s); $^{13}$C{$^1$H} NMR (d$_6$-C$_6$H$_6$, 75 MHz): 82.3 (d) J$_{C\text{-}P}$=55.4 Hz, 74.8 (t) J$_{C\text{-}P}$=2.9 Hz, 72.8 (m); 31p NMR (d$_6$-C$_6$H$_6$, 121 MHz): 163.7 (s); MS (EI, pos. ions): m/z=386 [M$^+$] (49%), 351 [M$^+$-Cl] (17%), 258 (5%), 223 (5%), 159 (24%), 130 (100%), 95 (58%), 69 (19%); EA: C: 30.69% (calc. 30.97%), P: 16.13% (calc. 15.97%), H: 2.15% (calc. 2.08%).

EXAMPLE 3

Direct synthesis of 1,1'-bis[dichlorophosphino] ferrocene (X) without isolation of intermediates At room temperature, 40.69 g (0.2186 mol) of ferrocene in 400 ml of abs. hexane is charged in a vessel. A mixture of 342 ml (0.547 mol) of 1.60 M n-butyllithium solution in hexane and 82.0 ml (63.6 g, 0.547 mol) of abs. N,N,N',N'-tetramethylethylenediamine is added dropwise at room temperature within 6 h. The mixture is allowed to stir at room temperature for 18 h. The supernatant is filtered off through an immersion frit, and the orange filtration residue is suspended in 400 ml of abs. THF. At –78° C., a solution of 95.0 ml (94.6g, 0.481 mol) of bis(diethylamino)chlorophosphine in 200 ml of abs. THF is added dropwise within 4 h. The mixture is allowed to thaw to room temperature and stirred for another 15 h. The solution, which has now a red-brown color, is cooled down to –78° C., and 390 ml of 5.6 M HCl in diethyl ether is added dropwise within 5 h. After warming up to room temperature, the solvent is distilled off completely, and the residue is taken up in 2 l of diethyl ether, and the solution filtrated from insolubles through a P4 frit with Celite 545® as a filtering aid. The clear filtrate is again completely freed from solvent. The red-brown solid is finally recrystallized from 200 ml of toluene/pentane at –20° C.. After drying in an oil pump vacuum, 52.82 g of a coarse-crystalline solid (0.136 mol, 62%) is obtained. Analytical results: appropriate (see Example 2).

EXAMPLE 4

Synthesis of (R,R)-1,1'-bis{dinaphtho[1,2-d;1,2-f] [1,3,2]dioxaphosphepin-8-yl}ferrocene (II, R$^1$=R$^2$= R$^3$=R$^4$=R$^5$=R$^6$=H)

1.28 g (3.30 mmol) of 1,1'-bis(dichlorophosphino) ferrocene (X) is dissolved in 250 ml of abs. toluene together with 1.89 g (6.60 mmol) of (R)-binaphthol (>99.9% ee), followed by heating under reflux for 36 h. Subsequently, the solvent is removed completely, and the residue is dissolved in 150 ml of boiling toluene. After cooling to room temperature, the solution is separated from insolubles by filtration through a P4 frit with Celite 545® as a filtering aid. The clear orange filtrate is concentrated to 25 ml and covered with a layer of 80 ml of abs. pentane. Over night, a fine-crystalline orange-brown solid precipitates, which is then filtered off and dried in an oil pump vacuum to obtain 2.70 g (2.98 mmol, 90%) of a fine-crystalline orange-brown solid. The product contains 1 mol of toluene per mole of substance. Analytical results: $^1$H NMR (d$_2$-CH$_2$Cl$_2$, 300 MHz): 7.88–7.72 (m) [6H], 7.64 (s) [1H], 7.61 (s) [1H], 7.44 (s) [1H], 7.41 (s) [1H], 7.37–7.23 (m) [8H], 7.22–7.12 (m) [6H], 7.11–7.02 (m) [3H], 6.81 (s) [1H], 6.78 (s) [1H], 4.63 (m) [2H], 4.50 (s) [2H], 4.23 (m) [2H], 3.64 (m) [2H], 3.64 (s) [3H] PhCH$_3$ (evaluation with toluene); $^{13}$C{$^1$H} NMR (d$_2$-CH$_2$Cl$_2$, 75 MHz): 149.38 (s), 148.3 (s), 132.0 (s), 131.7 (s), 130.7 (s), 130.2 (s), 128.5 (s), 127.6 (s), 127.5 (s), 127.3 (s), 125.80 (s), 125.78 (s), 125.2 (s), 124.4 (s), 124.1 (s), 123.9 (s), 123.7 (m), 122.6 (s), 121.4 (s), 120.8 (s), 76.1 (m), 72.9 (m), 72.3 (t) J=4.1 Hz, 71.5 (s), 69.7 (s) (evaluation without toluene); $^{31}$p NMR (d$_2$-CH$_2$Cl$_2$, 121 MHz): 190.8 (s); MS (EI, pos. ions): m/z=814 [M$^+$] (100%), 499 (7%), 435 (14%), 419 (12%), 268 (10%), 167 (12%); IR (KBr): $\tilde{v}$ (cm$^{-1}$)=3056 (w), 1617 (w-m), 1586 (m), 1505 (m), 1462 (m-s), 1430 (w), 1228 (s) vAr-O, 948 (s) vP-O, 820 (s), 798 (m-s), 780 (m-s), 751 (s), 684 (m), 636 (m-w), 573 (m), 552 (m), 497 (m); EA: C: 75.39% (75.50% calc.), H: 4.58% (4.45% calc.).

The crude product obtained may also be recrystallized from dichloromethane; it is then obtained in the form of a fine-crystalline orange solid (containing 1.5 mol of dichloromethane per mole of substance; analytical results: appropriate).

EXAMPLE 5

Synthesis of (S,S)-1,1'-bis{dinaphtho[1,2-d;1,2-f][1, 3,2]dioxaphosphepin-8-yl}ferrocene (II, R$^1$=R$^2$= R$^3$=R$^4$=R$^5$=R$^6$=H)

Using (S)-binaphthol, the same protocol as in Example 3 is otherwise used to obtain 2.70 g (2.98 mmol, 90%;

calculated as a toluene adduct) of the (S,S) product. Analytical results: NMR, MS and IR as in Example 3.

EXAMPLE 6

Synthesis of (R,R)-1,1'-bis(dinaphtho[1,2-d; 1,2-f][1,3,2]dioxaphosphepin-8-yl)ferrocene (II, $R^1=R^2=R^3=R^4=R^5=R^6=H$), starting from 1,1'-bis-[bis(diethylamino)phosphino]ferrocene (IX, R=Et)

In an oil pump vacuum, 1.000 g of strongly acidic aluminum oxide is heated thoroughly to the point of glowing. After cooling, 1.471 g (2.773 mmol) of 1,1'-bis[bis(diethylamino)phosphino]ferrocene (IX, R=Et) and 1.710 g (5.546 mmol) of (R)-binaphthol and 75 ml of abs. toluene are added. The mixture is heated at reflux for 20 days. After cooling, insolubles are filtered off, and the filtrate is freed from solvent to obtain 1.011 g (1.115 mmol, 40%) of an orange solid for which the analytical results after recrystallization are appropriate (see Example 3).

EXAMPLE 7

Synthesis of (R,R)-1,1'-bis{3,3'-dimethyldinaphtho[1,2-d;1,2-f][1,3,2]dioxaphosphepin-8-yl}ferrocene (II, $R^1=CH_3$, $R^2=R^3=R^4=R^5=R^6=H$)

0.772 g (1.99 mmol) of 1,1'-bis(dichlorophosphino)ferrocene (X) is dissolved in 50 ml of abs. toluene together with 1.407 g (3.981 mmol) of (R)-3,3'-dimethylbinaphthol hemibenzenate (>99.9% ee), followed by heating under reflux for 23 days. Subsequently, the solvent is removed completely, and the residue is dissolved in 10 ml of toluene. After cooling to room temperature, insolubles are filtered off, and the clear orange filtrate is covered with a layer of 40 ml of abs. pentane. The desired product is obtained in the form of a partly crystalline orange-brown solid, which is filtered off and dried in an oil pump vacuum to obtain 1.542 g (1.601 mmol, 80%) of an orange-brown solid. The product contains 1 mol of toluene per mole of substance. $^1$H NMR ($d_2$-$CH_2Cl_2$, 300 MHz): 7.78–7.63 (m) [6H], 7.47 (s) [2H], 7.34–7.20 (m) [4H], 7.18–6.98 (m) [13H], 4.76 (m) [2H], 4.55 (m) [2H], 4.25 (m) [2H], 3.57 (m) [2H], 2.46 (s) [3H], 2.24 (s) [3H]$PhCH_3$, 1.79 (s) [3H] (evaluation with toluene); $^{13}$C{$^1$H} NMR ($d_2CH_2Cl_2$, 75 MHz): 148.2 (s), 147.7 (s), 137.2 (s) ($PhCH_3$), 130.9 (s), 130.58 (s), 130.55 (s), 130.2 (s), 129.8 (s), 129.3 (s), 129.2 (s), 128.3 (s), 128.2 (s), 127.4 (s), 126.8 (s), 126.7 (s), 125.8 (s), 125.7 (s), 124.5 (s), 124.4 (s), 124.2 (s), 124.1 (s), 123.9 (s), 123.8 (s), 122.6 (s), 21.5 (s) ($PhCH_3$), 17.7 (s), 17.4 (s); ($d_1$-$CHCl_3$, 75 MHz): ca. 77.6 (m, X nucleus of an ABX spin system), 73.4 (m, X nucleus of an ABX spin system), 72.6 (m), 72.4 (s), 70.2 (s) (evaluation without toluene); $^{31}$P NMR ($d_2$-$CH_2Cl_2$, 121 MHz): 187.2 (s). MS (ESI, pos. ions): m/z=870 [M$^+$] (100%), 527 (9%), 463 (33%), 447 (20%), 435 (11%), 296 (13%), 280 (10%), 167 (21%).

By using o-xylene as the solvent, the reaction time can be reduced to 4 days (1.60 mmol of starting materials, 62% yield after recrystallization, analytical results are appropriate).

EXAMPLE 8

Synthesis of (R,R,R,R)-1,1'-bis(4,5-diphenyl-1,3,2-dioxaphospholane-2-yl)ferrocene (I, $R^1=R^2=Ph$)

At −78° C., 651 mg (3.04 mmol) of (R,R)-hydrobenzoin is charged in a vessel together with 1.0 ml of abs. triethylamine (6.63 mmol) in 150 ml of abs. toluene. A solution of 425 mg (0.80 mmol) of 1,1'-bis(dichlorophosphino)ferrocene (X) in 25 ml of abs. THF is added dropwise within 2 h. Then, thawing is allowed slowly in a cooling bath over night with stirring. The solution obtained is completely freed from solvent, and the orange solid is taken up in 200 ml of abs. diethyl ether. Insolubles are separated off by filtration through a P4 frit with Celite 545® as a filtering aid. The clear orange filtrate is completely freed from solvent to obtain an orange solid. Analytical results: $^1$H NMR ($d_8$-THF, 300 MHz): 7.40 (s) [8H], 7.36–7.30 (m) [6H], 7.29–7.23 (m) [4H], 7.22–7.11 (m) [6H], 5.05 (d) $J_{H-P}$=8.1 Hz [2H], 4.95 (d) $J_{H-P}$=9 Hz [2H], 4.82–4.60 (m) [8H]; $^{31}$P NMR ($d_8$-THF, 121 MHz): 181.7 (s).

EXAMPLE 9

Synthesis of (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$)

At −78° C., 14.7 ml (0.24 mmol) of a 16.4 mM solution of $Rh(cod)_2BF_4$ in abs. dichloromethane is charged in a vessel. Using a syringe pump, a solution of 219 mg (0.242 mmol) of (R,R)-1,1'-bis{dinaphtho[1,2-d;1,2-f][1,3,2]dioxaphosphepin-8-yl}ferrocene toluene adduct (II, $R^1=R^2=R^3=R^4=R^5=R^6=H$) in 20 ml of abs. dichloromethane is added dropwise. After the addition is complete, the mixture is allowed to warm to room temperature and stirred over night. The solution obtained is concentrated to 7 ml, and 50 ml of abs. pentane is quickly added with stirring. A light-yellow solution with an orange solid suspended therein is obtained. The supernatant is filtered off, and the solid obtained is dried in an oil-pump vacuum to obtain 245 mg (0.20 mmol, calculated as a $CH_2Cl_2$ adduct, yield: 85%) of an orange powdery solid (calculated as a $CH_2Cl_2$ adduct, yield: 85%). Analytical results: $^1$H NMR (d-$CHCl_3$, 300 MHz): 8.19 (s) [4H], 7.99 (s) [1H], 7.96 (s) [1H], 7.83 (s) [1H], 7.80 (s) [1H], 7.73 (s) [1H], 7.70 (s) [1H], 7.53–7.35 (m) [4H], 7.35–7.21 (m) [8H], 7.05 (s) [1H], 7.02 (s) [1H], 6.41 (t) $J_{H-P}$=7 Hz [2H], 5.10 (m) [2H], 4.59 (m) [2H], 4.19 (d) $J_{H-P}$=1 Hz, 3.94 (m) [2H], 3.84 (s) [2H], 2.83–2.20 (m) [6H], 1.85–1.58 (m) [2H]; $^{13}$C{$^1$H} NMR ($d_2$-$CH_2Cl_2$, 75 MHz): 133.3 (s), 133.1 (s), 132.8 (s), 132.5 (s), 132.4 (s), 131.5 (s), 129.6 (s), 129.5 (s), 128.1 (s), 127.7 (s) [2C], 127.3 (s), 127.0 (s), 126.6 (s), 124.3 (s), 123.4 (s), 122.0 (s), 121.8 (s), 112.2 (q) $J_{C-P}$=5 Hz, 106.6 (q) $J_{C-P}$=6.5 Hz, 78.1 (t) $J_{C-P}$=6.5 Hz, 77.8 (t) $J_{C-P}$=16.2 Hz, 74.7 (s), 74.4 (s), 34.1 (s), 27.8 (s); $^{31}$P NMR ($d_2$-$CH_2Cl_2$, 81 MHz): 169.4 (d) $^1J_{P-Rh}$=212.7 Hz; MS (ESI, pos. ions): m/z =1025 [1112-$BF_4$], 917 [M$^+$-COD]; IR (KBr): $\tilde{v}$ (cm$^{-1}$)=3056 (w), 2947 (w), 2920 (w), 2920 (w), 2879 (w), 2829 (w), 1586 (m), 1507 (m), 1462 (m), 1424 (m-w), 1361 (w), 1321 (m), 1222 (s), 1185 (s-m), 1068 (s), 1051 (s), 1033 (s), 944 (s), 825 (s), 806 (s), 771 (m), 691 (m), 558 (m-s); EA: C: 59.10% (calc. 59.80%), P: 5.41% (calc. 5.17%), H: 3.95% (calc. 3.87%), Rh: 8.98% (calc. 8.59%), Cl: 5.49% (calc. 5.92%); calculated values are based on the mono-$CH_2Cl_2$ adduct.

EXAMPLE 10

Synthesis of (S,S)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$)

Using (S,S)-1,1'-bis{dinaphtho[1,2-d; 1,2-f][1,3,2]dioxaphosphepin-8-yl}ferrocene, the same protocol as in Example 6 is otherwise used to obtain 246 mg (0.20 mmol) of an orange solid (85%)

EXAMPLE 11

Synthesis of (R,R)-1,1'-bis{dinaphtho[1,2-d;1,2-f][1,3,2]dioxaphosphepin-8-yl}ferrocene-$\eta^2$:$\eta^2$-1,5-cyclooctadieneiridium(I) hexafluorophosphate (XX, $R^1=R^2=R^3=R^4=R^5=R^6=H$)

324 mg (0.36 mmol) of (R,R)-1,1'-bis{dinaphtho[1,2-d;1,2-f][1,3,2]dioxaphosphepin-8-yl}ferrocene toluene adduct (II, $R^1=R^2=R^3=R^4=R^5=R^6=H$) is dissolved in 20 ml of abs. dichloromethane, and the solution is added dropwise, using a syringe pump, to a solution, cooled down to −78° C., of 212 mg (0.35 mmol) of bis(pyridine)-$\eta^2$:$\eta^2$-1,5-cyclooctadieneiridium(I) hexafluorophosphate in 20 ml of abs. dichloromethane. The mixture is allowed to warm to room temperature slowly over night, and the solvent is removed completely. The greenish solid obtained is washed with 20 ml of abs. diethyl ether to obtain 400 mg of a greenish solid (0.32 mmol, 91%). Analytical results: $^1$H NMR (d$_2$-CH$_2$Cl$_2$, 300 MHz): 8.14 (s) [1H], 8.11 (s) [1H], 8.03–7.93 (m) [4H], 7.88(s) [1H], 7.85 (s) [1H], 7.82 (s) [1H], 7.77 (s) [1H], 7.52–7.40 (m) [6H], 7.35–7.17 (m) [ca. 6H], 7.01 (s) [1H], 6.98 (s) [1H], 6.28 (m) [2H], 5.03 (m) [2H], 4.64 (m) [2H], 4.24 (m) [2H], 3.89 (m) [2H], 3.59 (m) [2H], 2.47–2.22 (m) [5H], 1.80–1.49 (m) [3H]; $^{31}$P NMR (d$_2$-CH$_2$Cl$_2$, 121 MHz): 136.5 (s).

EXAMPLE 12

Synthesis of (R,R)-1,1'-bis{dinaphtho[1,2-d; 1,2-f][1,3,2]dioxaphosphepin-8-yl}ferrocenechloro-$\eta^6$-1,4-cymeneruthenium(II) chloride (XVI, $R^1=R^2=R^3=R^4=R^5=R^6=H$)

162 mg (0.18 mmol) of (R,R)-1,1'-bis{dinaphtho[1,2-d;1,2-f][1,3,2]dioxaphosphepin-8-yl}ferrocene toluene adduct (II, $R^1=R^2=R^3=R^4=R^5=R^6=H$) is dissolved in 20 ml of abs. dichloromethane, and the solution is added dropwise, using a syringe pump, to 6,0 ml (0.09 mmol) of 15.5 mM a solution, cooled down to −78° C., of bis[$\eta^6$-1,4-cymeneruthenium(II) dichloride] (0.19 mmol of Ru) in abs. dichloromethane. The mixture is allowed to warm to room temperature slowly over night, and the solvent is removed completely. After drying in an oil pump vacuum, a red-brown solid is obtained.

EXAMPLE 13

Synthesis of (R,R)-1,1'-bis{dinaphtho[1,2-d;1,2-f][1,3,2]dioxaphosphepin-8-yl}ferrocenecopper(I) triflate (XXXII, $R^1=R^2=R^3=R^4=R^5=R^6=H$)

53.1 mg of 90% CuOTf.0.5 PhH (copper(I) triflate hemibenzenate, Tf=-SO$_2$CF$_3$) (0.19 mmol) is stirred in abs. dichloroethane over night at room temperature. At 10° C., 13 ml (0.20 mmol) of a 15 mM solution of (R,R)-1,1'-bis{dinaphtho[1,2-d;1,2-f][1,3,2]dioxaphosphepin-8-yl}ferrocene toluene adduct (II, $R^1=R^2=R^3=R^4=R^5=R^6=H$) in abs. dichloroethane is added dropwise to the CuOTf solution slowly using a syringe pump. The solution is stirred over night at room temperature, followed by filtering through a P4 frit. The clear dark-orange filtrate is covered with a layer of 30 ml of abs. pentane at room temperature. After 3 days at room temperature, the supernatant is filtered off, and the residual solid is dried in an oil pump vacuum to obtain a greenish-beige solid.

EXAMPLE 14

Protocol for the enantioselective hydrogenation of dimethyl itaconate with in situ prepared catalyst (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$)

To 8.0 ml of a 0.125 M substrate solution (dimethyl itaconate) in dichloromethane in a round-bottom flask with a lateral cock is added 1.0 ml of a 1.0 mM solution of Rh(cod)$_2$BF$_4$ in dichloromethane, followed by 1.1 ml of a 1.0 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. The solution is now saturated with hydrogen by three cycles of evacuating until the solvent slightly boils and refilling with hydrogen gas. Finally, the solution is subjected to a hydrogen pressure of 1.3 bar and stirred at room temperature for 20 h. For gas-chromatographical analysis of the product mixture, 2 ml of the thus obtained solution is filtered through 125 mg of silica (70–230 mesh, activity grade I). When hydrogenation is quantitative, an enantiomeric excess (ee) of 99.60% of the R-configuration product 2-methylsuccinic acid dimethyl ester is measured.

EXAMPLE 15

Protocol for the enantioselective hydrogenation of dimethyl itaconate with a preformed metal complex as a catalyst, (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium (I) tetrafluoroborate (XII, $R^1=R^2=R^3=R^4=R^5=R^6=H$)

To 8.0 ml of a 0.125 M substrate solution (dimethyl itaconate) in dichloromethane in a round-bottom flask with a lateral cock is added 1.0 ml of a 1.0 mM solution of (R,R)-1,1'-bis{dinaphtho[1,2-d; 1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$) in dichioromethane, followed by 1.0 ml of dichloromethane. The solution is now saturated with hydrogen by three cycles of evacuating until the solvent slightly boils and refilling with hydrogen gas. Finally, the solution is subjected to a hydrogen pressure of 1.3 bar and stirred at room temperature for 20 h. For gas-chromatographical analysis of the product mixture, 2 ml of the thus obtained solution is filtered through 125 mg of silica (70–230 mesh, activity grade I). When hydrogenation is quantitative, an enantiomeric excess (ee) of 99.6% of the R-configuration product 2-methylsuccinic acid dimethyl ester is measured.

EXAMPLE 16

Protocol for the enantioselective hydrogenation of dimethyl itaconate with in situ prepared catalyst (S,S)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$)

To 8.0 ml of a 0.125 M substrate solution (dimethyl itaconate) in dichloromethane in a round-bottom flask with a lateral cock is added 1.0 ml of a 1.0 mM solution of Rh(cod)$_2$BF$_4$ in dichloromethane, followed by 1.1 ml of a 1.0 mM solution of (S,S)-1,1'-bis{dinaphtho[1,2-d; 1,2-f][1,3,2]dioxaphosphepin-8-yl}ferrocene (II, $R^1=R^2=R^3=R^4=R^5=R^6=H$) in dichloromethane. The solution is now saturated with hydrogen by three cycles of evacuating until the solvent slightly boils and refilling with hydrogen gas.

Finally, the solution is subjected to a hydrogen pressure of 1.3 bar and stirred at room temperature for 20 h. For gas-chromatographic analysis of the product mixture, 2 ml of the thus obtained solution is filtered through 125 mg of silica (70–230 mesh, activity grade I). When hydrogenation is quantitative, an enantiomeric excess (ee) of 99.6% of the S-configuration product 2-methylsuccinic acid dimethyl ester is measured.

EXAMPLE 17

Protocol for the enantioselective hydrogenation of 2-acetamido-methyl acrylate with in situ prepared catalyst (R,R)-1,1'-bis{dinaphtho[1,2-d;1,2-f][1,3,2]dioxaphosphepin-8-yl}ferrocene-$\eta^2$: $\eta^2$-1,5-cyclooctadienerhodium(I) tetrafluoroborate (XII, $R^1=R^2=R^3=R^4=R^5=R^6=H$)

To 8.0 ml of a 0.125 M substrate solution (2-acetamidomethyl acrylate) in dichloromethane in a round-bottom flask with a lateral cock is added 1.0 ml of a 1.0 mM solution of $Rh(cod)_2BF_4$ in dichloromethane, followed by 1.1 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. The solution is now saturated with hydrogen by three cycles of evacuating until the solvent slightly boils and refilling with hydrogen gas. Finally, the solution is subjected to a hydrogen pressure of 1.3 bar and stirred at room temperature for 20 h. For gas-chromatographical analysis of the product mixture, 2 ml of the thus obtained solution is filtered through 125 mg of silica (70–230 mesh, activity grade I). When hydrogenation is quantitative, an enantiomeric excess (ee) of 99.6% of the R-configuration product N-acylalanine methyl ester is measured.

EXAMPLE 18

Same as Example 14, but with 2-acetamidoarylic acid methyl ester as the educt and R-configuration N-acetylalanine methyl ester as the product (quantitative conversion; ee=99.5%).

EXAMPLE 19

Protocol for the enantioselective hydrogenation of (Z)-2-acetamidocinnamic acid methyl ester with in situ prepared catalyst (R,R)-1,1'-bis{dinaphtho[1,2-d; 1,2-f][1,3,2]dioxaphosphepin-8-yl}ferrocene-$\eta^2$:$\eta^2$-1,5-cyclooctadienerhodium(I)tetrafluoroborate (XII, $R^1=R^2=R^3=R^4=R^5=R^6=H$)

To a round-bottom flask with a lateral cock, 1.0 ml of a 1.0 mM solution of $Rh(cod)_2BF_4$ in dichloromethane is added, followed by 1.1 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. To this, 8.0 ml of a 0.125 substrate solution (of (Z)-2-acetamidocinnamic acid methyl ester) in dichloromethane is added. The solution is now saturated with hydrogen by three cycles of evacuating until the solvent slightly boils and refilling with hydrogen gas. Finally, the solution is subjected to a hydrogen pressure of 1.3 bar and stirred at room temperature for 20 h. For gas-chromatographical analysis of the product mixture, 2 ml of the thus obtained solution is filtered through 125 mg of silica (70–230 mesh, activity grade I). When hydrogenation to give N-acylphenylalanine methyl ester is quantitative, an enantiomeric excess (ee) of 99% is measured. Determination of the enantiomeric excess (ee) was effected by HPLC with a chiral stationary phase.

EXAMPLE 20

Protocol for the enantioselective hydrogenation of (Z)-2-acetamidocinnamic acid with in situ prepared catalyst (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$)

To a 30 ml Schlenk vessel, 1.0 ml of a 1.0 mM solution of $Rh(cod)_2BF_4$ in dichloromethane is added, followed by 1.1 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. To this, 8.0 ml of a 0.125 M substrate solution ((Z)-2-acetamidocinnamic acid) in dichloromethane/iso-propanol 3:1 is added. The solution is transferred into a 50 ml V4A steel autoclave with a Teflon inset and manometer connecting tube, subjected to a hydrogen pressure of 20 bar, and stirred at room temperature for 20 h. After releasing the pressure from the autoclave, the whole solution is completely freed from solvent and analyzed by $^1H$ NMR spectroscopy to determine the conversion. Determination of the enantiomeric excess is effected by HPLC with a chiral stationary phase. When hydrogenation to give N-acylphenylalanine is quantitative, an enantiomeric excess (ee) of 99% is measured.

EXAMPLE 21

Protocol for the enantioselective hydrogenation of N-(1-phenylethylidene)aniline with in situ prepared catalyst (R,R)-1,1'-bis{dinaphtho[1,2-d; 1,2-f][1,3,2]dioxaphosphepin-8-yl}ferrocene-$\eta^2$:$\eta^2$-1,5-cyclooctadieneiridium(I) hexafluorophosphate (XX, $R^1=R^2=R^3=R^4=R^5=R^6=H$, $X=PF_6$).

To a 30 ml Schienk vessel, 1 ml of a 1.0 mM solution of $(Py)_2Ir(cod)PF_6$ in dichloromethane is added, followed by 1.1 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. To this, 8.0 ml of a 0.125 M substrate solution (N-(1-phenylethylidene)aniline) in dichloromethane is added. The solution is transferred into a 50 ml V4A steel autoclave with a Teflon inset and manometer connecting tube, subjected to a hydrogen pressure of 100 bar, and stirred at room temperature for 24 h. After releasing the pressure from the autoclave, 2 ml of the thus obtained solution is filtered through 125 mg of silica (70–230 mesh, activity grade I). Determination of the conversion is effected by gas chromatography, and the enantiomeric excess is determined by HPLC with a chiral stationary phase. When hydrogenation to give N-phenyl-1-phenylethylamine is quantitative, an enantiomeric excess (ee) of 63% is measured.

EXAMPLE 22

Protocol for the enantioselective hydrogenation of α-acetamidostyrene with in situ prepared catalyst (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$).

To a 30 ml Schlenk vessel, 2.0 ml of a 1.0 mM solution of $Rh(cod)_2BF_4$ in dichloromethane is added, followed by 2.2 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane. To this, 8.0 ml of a 0.125 M substrate solution (α-acetamidostyrene) in dichloromethane is added. The solution is transferred into a 50 ml V4A steel autoclave with a Teflon inset and manometer connecting tube, subjected to a hydrogen pressure of 80 bar, and stirred at room temperature for 20 h. After releasing the pressure from the autoclave, the whole solution is completely freed from solvent and analyzed by $^1$H NMR spectroscopy to determine the conversion. Determination of the enantiomeric excess is effected by HPLC with a chiral stationary phase. When hydrogenation to give N-acyl-1-phenylethylamine is quantitative, an enantiomeric excess (ee) of 96% is measured.

EXAMPLE 23

Same as Example 22, but with only 1.0 ml of a 1.0 mM solution of Rh(cod)$_2$BF$_4$ in dichloromethane and 1.1 ml of a 1 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in dichloromethane; for a conversion of >99%, this resulted in an enantiomeric excess (ee) of >92%.

EXAMPLE 24

Protocol for the enantioselective hydroboration of styrene with in situ prepared catalyst (R,R)-1,1'-bis{dinaphtho[1,2-d; 1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^4=R^5=R^6=H$)

To a 30 ml Schlenk vessel, 1.0 ml of a 10 mM solution of Rh(cod)$_2$BF$_4$ in dichloromethane is added, followed by 1.1 ml of a 10 mM solution of (R,R)-1,1'-bis{dinaphtho[1,2-d;1,2-f][1,3,2]dioxaphosphepin-8-yl}ferrocene (II, $R^1=R^2=R^3==R^4R^5=R^6=H$) in dichloromethane. After removing the solvent, 2.0 ml of a 0.5 M solution of styrene in dimethoxyethane (DME) is added, and the solution obtained is cooled down to −80° C. To this solution, 1.0 ml of a 3 M solution of catecholborane in DME is added, and the reaction mixture is stirred at −80° C.

The reaction is stopped after 22 h by adding 1 ml of methanol and allowing to warm to room temperature. The mixture is cooled down to 0° C., and 2 ml of 3 M aqueous NaOH and 0.5 ml of 30% aqueous H$_2$O$_2$ is added successively. After allowing to warm to room temperature, 25 ml of distilled water and 30 ml of dichloromethane are added, and the phases are separated. The aqueous phase is extracted three times with 25 ml each of dichloromethane. The organic phases are combined and partitioned two times each with 30 ml of 1 M aqueous NaOH and then saturated aqueous NH$_4$Cl. Finally, the solution is dried over magnesium sulfate and freed from solvent. Determination of the conversion and enantiomeric excess (ee) was effected by gas chromatography. When the conversion was quantitative, an enantiomeric excess (ee) of 87% and a selectivity (over the formation of 2-phenylethanol) of 97% for (R)-1-phenylethanol could be determined.

EXAMPLE 25

Same as Example 24, but at a temperature of −30° C.; at 100% conversion and 83% yield (1-phenylethanol, determined in comparison with n-tetradecane as a GC internal standard, taking FID response factors into account), this resulted in an enantiomeric excess (ee) of 84% and a selectivity (over the formation of 2-phenylethanol) of 93% for (R)-1-phenylethanol.

EXAMPLE 26

Same as Example 24, but at room temperature; at 100% conversion and 79% yield (1-phenylethanol, determined in comparison with n-tetradecane as a GC internal standard, taking FID response factors into account), this resulted in an enantiomeric excess (ee) of 72% and a selectivity (over the formation of 2-phenylethanol) of 90% for (R)-1-phenylethanol.

EXAMPLE 27

Same as Example 24, but using the preformed metal complex (R,R)-1,1'-bis{dinaphtho[1,2-d;1,2-f][1,3,2]dioxaphosphepin-8-yl}ferrocene-$\eta^2$:$\eta^2$-1,5-cyclooctadienerhodium(I) tetrafluoroborate (XII, $R^1=R^2=R^3=R^4=R^5=R^6=H$) as a catalyst (charged as a 10 mM solution (1.0 ml) in dichloromethane instead of the in situ prepared solution); at a complete conversion and 85% yield (1-phenylethanol, determined in comparison with n-tetradecane as a GC internal standard, taking FID response factors into account), this resulted in an enantiomeric excess (ee) of 88% and a selectivity (over the formation of 2-phenylethanol) of 96% for (R)-1-phenylethanol.

EXAMPLE 28

Protocol for the enantioselective 1,4-addition of diethylzinc to 2-cyclohexene-1-one with in situ prepared catalyst bis{(R,R)-1,1'-bis{dinaphtho[1,2-d;1,2-f][1,3,2]dioxaphosphepin-8-yl}ferrocene}copper(II) triflate (XXXVI, $R^1=R^2=R^3=R^4=R^5=R^6=H$)

To a 30 ml Schlenk vessel, 1.0 ml of a 10 mM solution of Cu(OTf)$_2$ in tetrahydrofuran is added at room temperature, followed by 2 ml of a 10 mM solution of (R,R)-1,1'-bis{dinaphtho[1,2-d;1,2-f][1,3,2]dioxaphosphepin-8-yl}ferrocene (II, $R^1=R^2=R^3=R^4=R^5=R^6=H$) in tetrahydrofuran. After stirring at room temperature for 30 min, the solution obtained is cooled down to −30° C., and 1.0 ml of a 1 M solution of 2-cyclohexene-1-one in THF is added. To this solution, 1.0 ml of a 1.5 M solution of diethylzinc in tetrahydrofuran is added, and the reaction mixture is stirred at −30° C.

After 20 h, the reaction is stopped by adding 10 ml of about 1.3 M aqueous HCl, and the mixture is taken to 0° C. After the addition of 20 ml of distilled water and 30 ml of dichloromethane, the phases are separated at room temperature, and the aqueous phase is partitioned three times with 20 ml each of dichloromethane. After drying over magnesium sulfate, the solvent is removed completely, and the raw product is taken up in 2 ml of dichloromethane. Determination of the conversion and enantiomeric excess (ee) is effected by gas chromatography, yielding an ee of 95% for complete conversion. The product of a 1,2-addition was not formed.

EXAMPLE 29

Same as Example 28, but using 2-cycloheptene-1-one (95% purity) instead of 2-cyclohexene-1-one; at 92% conversion, this resulted in an enantiomeric excess (ee) of 84%. The product of a 1,2-addition was not formed.

What is claimed is:

1. Chiral C$_2$-symmetric diphosphonites comprising ferrocene as a backbone, characterized by containing either chiral C$_2$-symmetric 1,2-diols with an aliphatic basic structure or axially chiral aromatic or heteroaromatic diols in a P/O heterocycle.

2. The diphosphonites according to claim 1, being optically pure and pure with respect to diastereomers.

3. The diphosphonites according to claim 1, their structure corresponding to general formula I

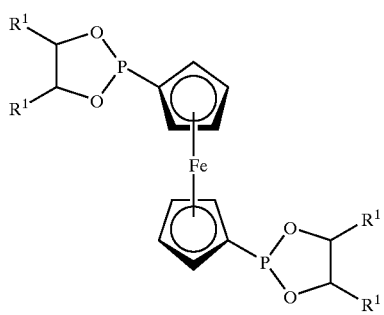

wherein R¹ is a saturated hydrocarbon which may optionally be functionalized, a non-aromatic unsaturated hydrocarbon which may optionally be functionalized, an aromatic or heteroaromatic group which may optionally be functionalized, an ester (—CO₂R) or an amide (—C(O)NRR'), wherein R and R' represent substituents which are hydrogen, saturated or non-aromatic unsaturated hydrocarbons which may optionally be functionalized, or aromatic residues which may optionally be functionalized.

4. The diphosphonites according to claim 3, wherein R¹ represents phenyl, 1-naphthyl, 2-naphthyl, carboxypropyl, carboxy-iso-propyl, carboxybutyl, carboxy-tert-butyl, carboxyneopentyl or carboxyphenyl.

5. The diphosphonites according to claim 1, their structures corresponding to general formula II or III

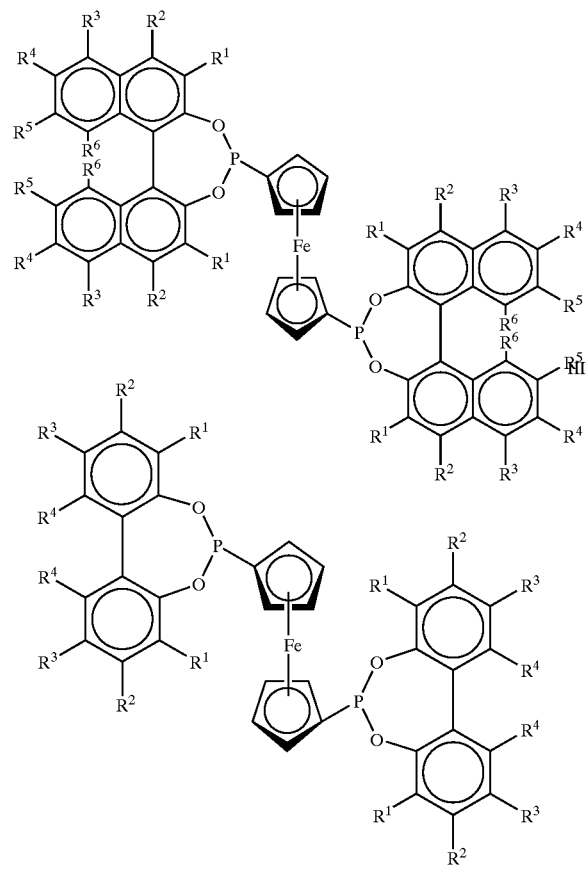

with residues R¹, R², R³, R⁴, R⁵ and R⁶, which may independently represent the following groups: hydrogen (—H), saturated hydrocarbons which may optionally be functionalized and/or bridging, aromatic or heteroaromatic groups which may optionally be functionalized and/or condensed, non-aromatic unsaturated hydrocarbons which may optionally be functionalized, silyl groups, halogens (—Cl, —Br, —F or —I), nitro (—NO₂) or nitrile (—CN) groups, or esters (—CO₂R), amides (—C(O)NRR'), amines (—NRR'), ethers (—OR), sulfides (—SR) or selenides (—SeR), wherein R and R' represent substituents selected from hydrogen, saturated or non-aromatic unsaturated hydrocarbons which may optionally be functionalized, or aromatic residues which may optionally be functionalized.

6. The diphosphonites according to claim 5, their structures corresponding to general formula II with R¹=R²=R³=R⁴=R⁵=R⁶=H.

7. The diphosphonites according to claim 5, their structures corresponding to general formula II with R²=R³=R⁴=R⁵=R⁶=H and a residue R¹ which may represent methyl, ethyl, n-propyl, iso-propyl, tert-butyl, phenyl, 2,5-dimethylphenyl, 2,5-di-tert-butylphenyl, —NO₂, —Br, —SiR₃, —C≡C—R, —C≡C—SiR₃, —CO₂R or —NR₂, wherein R is a saturated hydrocarbon or aromatic residue.

8. The diphosphonites according to claim 5, their structures corresponding to general formula III with R¹=R²=H and R³+R⁴=—(CH₂)₄—.

9. The diphosphonites according to claim 5, their structures corresponding to general formula III wherein R²=H, R³+R⁴=—(CH₂)₄—, and a residue R¹ which may represent methyl, ethyl, n-propyl, iso-propyl, tert-butyl, phenyl, 2,5-dimethylphenyl, 2,5-di-tert-butylphenyl, —NO₂, —SiR₃, —C≡C—R, —C≡C—SiR₃, —CO₂R or —NR₂, wherein R is a saturated hydrocarbon or aromatic residue.

10. The diphosphonites according to claim 1, their structures corresponding to general formula IV

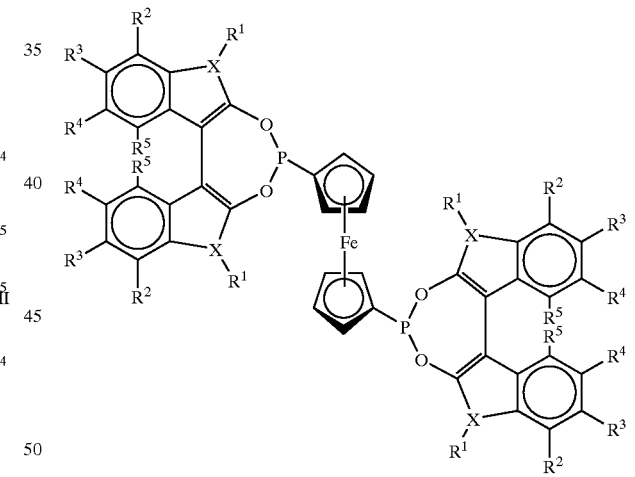

with X=nitrogen, sulfur or oxygen, and residues R¹ (only for X=N), R², R³, R⁴ and R⁵ which may independently represent the following groups: hydrogen (—H), saturated hydrocarbons which may optionally be functionalized and/or bridging, aromatic or heteroaromatic groups which may optionally be functionalized and/or condensed, non-aromatic unsaturated hydrocarbons which may optionally be functionalized, silyl groups, halogens (—Cl, —Br, —F or —I), nitro (—NO₂) or nitrile (—CN) groups, or esters (—CO₂R), amides (—C(O)NRR'), amines (—NRR'), ethers (—OR), sulfides (—SR) or selenides (—SeR), wherein R and R' represent substituents selected from hydrogen, saturated or non-aromatic unsaturated hydrocarbons which may optionally be functionalized, or aromatic residues which may optionally be functionalized.

11. A process for the preparation of chiral $C_2$-symmetric diphosphonites comprising ferrocene as a backbone according to claim 1, wherein 1,1'-ferrocenylenediphosphonous acid tetraamides with structures corresponding to general formula IX

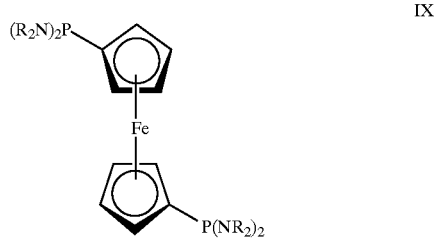

are reacted with an appropriate diol.

12. A process for the preparation of chiral $C_2$-symmetric diphosphonites comprising ferrocene as a backbone according to claim 1, wherein 1,1'-bis(dichlorophosphino) ferrocene is reacted with an appropriate diol without adding further reagents or catalysts.

13. Chiral transition metal complexes consisting of a diphosphonite according to claim 1 and a transition metal of Periodic Table groups VIIb, VIII or Ib.

14. The transition metal complexes according to claim 13 of general formula XI to XXXVIII

| [I.Rh(cod)X] (XI) | [II.Rh(cod)X] (XII) | [III.Rh(cod)X] (XIII) | [IV.Rh(cod)X] (XIV) |
|---|---|---|---|
| [I.Ru(cymol)Cl]X (XV) | [II.Ru(cymol)-Cl]X (XVI) | [III.Ru(cymol)-Cl]X (XVII) | [IV.Ru(cymol)-Cl]X (XVIII) |
| [I.Ir(cod)X] (XIX) | [II.Ir(cod)X] (XX) | [III.Ir(cod)X] (XXI) | [IV.Ir(cod)X] (XXII) |
| [I.Ni(cod)] (XXIII) | [II.Ni(cod)] (XXIV) | [III.Ni(cod)] (XXV) | [IV.Ni(cod)] (XXVI) |
| [I.Pd(CH$_3$)$_2$] (XXVII) | [II.Pd(CH$_3$)$_2$] (XXVIII) | [III Pd(CH$_3$)$_2$] (XXIX) | [IV.Pd(CH$_3$)$_2$] (XXX) |
| [I.CuOTf] (XXXI) | [II.CuOTf] (XXXII) | [III.CuOTf] (XXXIII) | [IV.CuOTf] (XXXIV) |
| [I.Cu(OTf)$_2$] (XXXV) | [II.Cu(OTf)$_2$] (XXXVI) | [III.Cu(OTf)$_2$] (XXXVII) | [IV.Cu(OTf)$_2$] (XXXVIII) | wherein X may represent the following anions: tetrafluoroborate, hexafluorophosphate, hexafluoroantimonate (V) or $BAr_4^-$, wherein Ar is phenyl or 2,5-bis(trifluoromethyl)phenyl, cod standing for $\eta^2{:}\eta^2$-1,5-cyclooctadiene, cymol standing for $\eta^6$-1-iso-propyl-4-methylbenzene in formulae XI to XXXVIII and Tf standing for triflate.

15. A process comprising enantioselective hydrogenation of an olefin, ketone or imine in the presence of a chiral transition metal complex according to claim 13.

16. The process according to claim 15, wherein the transition metal complex employed is selected from those of general formulae XI to XXII wherein X may represent the following anions: tetrafluoroborate, hexafluorophosphate, hexafluoroantimonate (V) or $BAr_4^-$, wherein Ar is phenyl or 2,5-bis(trifluoromethyl)phenyl, cod standing for $\eta^2{:}\eta^2$-1,5-cyclooctadiene and cymol standing for $\eta^6$-1-iso-propyl-4-methylbenzene in formulae XI to XXII.

17. A process comprising enantioselective hydroboration of an olefin in the presence of a chiral transition metal complex according to claim 14, wherein the transition metal complex employed is selected from those of general formulae XI to XIV and XIX to XXII.

18. A process comprising enantioselective 1,4-addition to an activated olefin in the presence of a chiral transition metal complex according to claim 14, wherein the transition metal complex employed is selected from those of general formulae XXI to XXXVIII.

19. The process according to claim 18, wherein $\alpha,\beta$-unsaturated ketones are employed as said activated olefin.

20. Chiral $C_2$-symmetric diphosphonates comprising ferrocene as a backbone, characterized by containing axially chiral aromatic or heteroaromatic diols in a P/O heterocycle.

21. Chiral transition metal complexes consisting of a diphosphonite according to claim 20 and a transition metal of Periodic Table groups VIIb, VIII or Ib.

22. A process comprising enantioselective hydrogenation of an olefin, ketone or imine in the presence of a chiral transition metal complex according to claim 21.

23. A process comprising enantioselective hydroboration of an olefin in the presence of a chiral transition metal complex according to claim 21.

24. A process comprising enantioselective 1,4-addition to an activated olefin in the presence of a chiral transition metal complex according to claim 21.

* * * * *